United States Patent [19]

Baran et al.

[11] 3,972,907
[45] Aug. 3, 1976

[54] ANTI-HYPERLIPIDEMIC FATTY ACIDS AND ESTERS

[75] Inventors: John S. Baran, Winnetka; Chi-Dean Liang, Glenview, both of Ill.

[73] Assignee: G. D. Searle & Co., Chicago, Ill.

[22] Filed: Mar. 24, 1975

[21] Appl. No.: 561,646

[52] U.S. Cl. .................... 260/410.9 R; 260/413; 424/312; 424/315
[51] Int. Cl.² ........................................ C11C 3/02
[58] Field of Search ............ 260/410.9 R, 410.9 N, 260/413; 424/312, 315

[56] References Cited
FOREIGN PATENTS OR APPLICATIONS
3,996  6/1967  South Africa

OTHER PUBLICATIONS

Merk Index Eighth Ed. p. 97.

*Primary Examiner*—Winston A. Douglas
*Assistant Examiner*—John F. Niebling
*Attorney, Agent, or Firm*—John A. Dhuey

[57] ABSTRACT

2,2-Dialkylated arachidonic acid and esters are prepared from the alkyl esters of arachidonic acid by treatment with the appropriate alkyl iodide. The compounds so produced are useful as pharmacological agents in view of their ability to inhibit lipogenesis.

7 Claims, No Drawings

ANTI-HYPERLIPIDEMIC FATTY ACIDS AND ESTERS

The present invention is concerned with derivatives of arachidonic acid. More particularly it is concerned with novel compounds of the formula

wherein $R_1$ is lower alkyl and $R_2$ is hydrogen or lower alkyl and the dotted lines represent optional double bonds.

Especially preferred are compounds of the formula

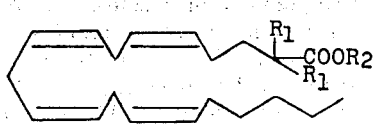

wherein $R_1$ and $R_2$ are defined as above.

For purposes of this invention, lower alkyl comprehends those radicals, straight or branched-chain, having 1–7 carbon atoms inclusive, typified by methyl, ethyl, propyl, isopropyl and the like.

The instant compounds having the 5, 8, 11 and 14 double bonds are prepared preferably by alkylating the appropriate alkyl ester of arachidonic acid with an alkyl iodide in the presence of a base, such as a secondary amine, and n-alkyl lithium, i.e. n-butyl lithium. Typically, ethyl arachidonate is added to n-isopropylcyclohexylamine containing n-butyl lithium at a low temperature, e.g. −78°C., and then methyl iodide is added to yield ethyl 2-methylarachidonate. That same procedure then is repeated with ethyl 2-methylarachidonate in place of ethyl arachidonate to yield ethyl 2,2-dimethylarachidonate. The ester moiety can be cleaved with lithium iodide in an aromatic amine, e.g. collidine, to yield the corresponding acid. For example, methyl 2,2-dimethylarachidonate, when treated with lithium iodide in collidine, affords 2,2-dimethyl arachidonic acid.

The 2,2-dialkylated-5,6,8,9-tetrahydroarachidonic acids and esters are prepared preferably by a series of reactions from linoleic acid. Linoleic acid is reduced, typically with a metallic hydride such as lithium aluminum hydride, to afford 9-cis,12-cis-octadecadienol, which is allowed to react subsequently with tosyl chloride to yield 1-tosyloxy-9-cis,12-cis-octadecadiene. Contacting that compound with sodium iodide affords 1-iodo-9-cis,12-cis-octadecadiene. Allowing the latter compound to react with a dialkyl alkylmalonate, e.g. diethyl methylmalonate affords the corresponding arachidonic acid derivatives, e.g. ethyl 2-carboethoxy-2-methyl-5,6,8,9-tetrahydroarachidonate. Hydrolysis, for example with 5% ethanolic potassium hydroxide, affords the 2-carboxyderivatives, e.g. 2-carboxy-2-methyl-5,6,8,9-tetrahydroarachidonic acid. Decarboxylation at the 2-carbon atom position is accomplished by heating in quinoline in the presence of a small amount of copper powder, thus yielding 2-methyl-5,6,8,9-tetrahydroarachidonic acid. The acid is esterified using the appropriate diazoalkane or alkyl iodide in dimethyl formamide, and the ester is alkylated with an alkyl halide in the presence of base and n-alkyl lithium to yield the instant alkyl 2,2-dialkyl-5,6,8,9-tetrahydroarachidonates.

When γ-linolenic acid is substituted above for linoleic acid, the same sequence of reactions affords the instant alkyl 2,2-dialkyl-5,6-dihydroarachidonates.

The compounds of this invention are useful as pharmachological agents in view of their unexpected potency in inhibiting lipogenesis. Inhibition of lipogenesis is determined in as assay described as follows:

ASSAY

Male Charles River rats (160–200 g.), having had free access to food and water, are administered a standard diet containing 2% DEAE-cellulose (Reeve Angel anion exchange resin) for 5 days. The rats then are sacrificed and their livers removed immediately. The livers are homogenized in a medium consisting of 0.1 M potassium phosphate, pH 7.4, 0.004 m $MgCl_2$ and 0.03 M nicotinamide, and the microsomalcytosol fraction obtained by centrifugation. 2.0 Ml. of the microsomal-cytosol fraction is incubated, at 37°C. for 90 minutes for fatty acid measurements and for measurement of cholesterol biosynthesis, in a standard assay mixture containing 10 micromoles of sodium acetate containing 0.1 microcuries of 2-$C^{14}$-acetate, 2 micromoles nicotinamide adenine dinucleotide, 2 micromoles nicotinamide adenine dinucleotide phosphate, and 20 micromoles glucose-6-phosphate, and test compound, initially at 0.001 M, is added. All assays are run in duplicate with the assay to which no test compound is added serving as a control. Heat inactivated homogenate serves as blank for both control and test systems.

Reaction rate is determined per unit of time by the amount of $C^{14}$ label incorporated into the lipid fraction from the radioactive acetate. Results are reported as % inhibition (i.e. (Reaction Rate for Test Compound/Reaction Rate for Control) x 100).

The invention will appear more fully from the examples which follow. They are not to be construed as limiting the invention in spirit or scope since numerous modifications in materials and methods will be apparent to those skilled in the art. In the examples which follow temperatures are presented in degrees centigrade (°C.).

EXAMPLE 1

To a solution of 1.7 g. of n-isopropylcyclohexylamine in 15 ml. of tetrahydrofuran, at −78°, is added 5.5 ml. of a 2.4 N n-butyl lithium n-hexane solution. Then 3 g. of ethyl arachidonate in 150 ml. of tetrahydrofuran is added dropwise, over a 2-hour period, at −78°. Then 1.5 ml. of methyl iodide is added and the mixture is allowed to warm to room temperature. The solution is concentrated by evaporating tetrahydrofuran, then extracted with ether to yield ethyl 2-methylarachidonate.

EXAMPLE 2

The ethyl 2-methylarachidonate produced in Example 1 is substituted for the ethyl arachidonate in Example 1 and the procedure of Example 1 is repeated to afford ethyl 2,2-dimethylarachidonate. That compound is represented structurally by the following formula

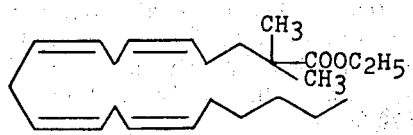

EXAMPLE 3

By substituting an equivalent quantity of methyl arachidonate in the procedure of Example 1, and proceeding in the manner described in Examples 1 and 2, there is produced methyl 2,2-dimethylarachidonate. That compound is represented structurally by the following formula

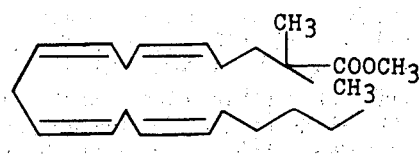

EXAMPLE 4

300 Mg. of methyl 2,2-dimethylarachidonate and 300 mg. of lithium iodide in 5 ml. of collidine are heated at 170° for 3 hours. Desired 2,2-dimethylarachidonic acid is recovered by preparative thin layer chromatography. That compound is represented structurally by the following formula

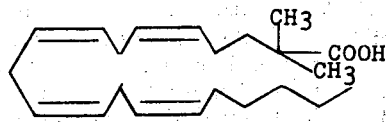

EXAMPLE 5

Substitution of an equivalent quantity of ethyl iodide in the procedure of Examples 1 and 2 affords ethyl 2,2-diethylarachidonate.

EXAMPLE 6

1.1 Part of linoleic acid in several milliliters of ethyl ether is added dropwise at room temperature to a solution consisting of 1 gram of lithium aluminum hydride in 100 ml. of anhydrous ethyl ether. That solution is allowed to stir for about 18 hours, then saturated ammonium chloride solution is added. Extraction with ethyl acetate affords 9-cis,12-cis-octadecadienol.

EXAMPLE 7

To a solution of 800 mg. of 9-cis,12-cis-octadecadienol in 30 ml. of pyridine, cooled in a Dry Ice-acetone bath, is added 1.5 grams of tosyl chloride. The solution is stirred for 5 minutes, then stirred in an ice water bath for about 24 hours. The reaction mixture is poured into ice water and extracted with ether to afford 1-tosyloxy-9-cis,12-cis-octadecadiene.

EXAMPLE 8

2.5 Grams of 1-tosyloxy-9-cis,12-cis-octadecadiene and 3.6 grams of sodium iodide are allowed to react in 75 ml. of boiling acetone for about 3 hours. The reaction mixture then is cooled, filtered and evaporated under a nitrogen atmosphere. The remaining material is taken up in ether, washed with sodium thiosulfate and water and dried. The product remaining is 1-iodo-9cis,12-cis-octadecadiene.

EXAMPLE 9

7.0 Grams of diethyl methylmalonate is dissolved in 100 ml. of n-butanol. Then 4.0 grams of potassium t-butoxide is added and the mixture is heated with stirring. 20 Ml. of the resulting slurry is added to 700 mg. of 1-iodo-9-cis,12-cis-octadecadiene and the mixture is heated at reflux for about 3 hours. Then the mixture is filtered to remove potassium iodide and concentrated under a nitrogen stream to remove the n-butanol solvent. The material remaining is ethyl 2-carboethoxy-2-methyl-5,6,8,9-tetrahydroarachidonate.

EXAMPLE 10

The material prepared in Example 9 is added to 50 ml. of 5% ethanolic potassium hydroxide and refluxed for about 25 hours. After extraction with a solvent system consisting of the upper layer of 100 ml. of 2 β-ethanol, 40 ml. of water and 200 ml. of n-pentane, there is afforded 2-carboxy-2-methyl-5,6,8,9-tetrahydroarachidonic acid.

EXAMPLE 11

800 Mg. of 2-carboxy-2-methyl-5,6,8,9-tetrahydroarachidonic acid is dissolved in 20 ml. of freshly distilled quinoline. A trace of copper powder is added and the solution is heated to 120° under a nitrogen stream. Heating is continued for about 2 hours, after which time the reaction mixture is poured into ice, acidified with dilute sulfuric acid in the presence of ice, extracted with ether, washed with water, dried over anhydrous sodium sulfate and concentrated under reduced pressure. The residual oil is dissolved in 30 ml. of cyclohexane and concentrated under reduced pressure to afford 2-methyl-5,6,8,9-tetrahydroarachidonic acid.

EXAMPLE 12

A solution of 500 mg. of 2-methyl-5,6,8,9-tetrahydroarachidonic acid, 3 ml. of dimethylformamide, 0.5 parts of sodium bicarbonate and 0.5 gm. of methyl iodide is allowed to stand for about 18 hours. Extraction with ether then affords methyl 2-methyl-5,6,8,9-tetrahydroarachidonate.

EXAMPLE 13

By substituting an equivalent quantity of methyl 2-methyl-5,6,8,9-tetrahydroarachidonate in the procedure of Example 1, there is afforded methyl 2,2-dimethyl-5,6,8,9-tetrahydroarachidonate.

EXAMPLE 14

By substituting an equivalent quantity of methyl 2,2-dimethyl-5,6,8,9-tetrahydroarachidonate in the procedure of Example 4, there is obtained 2,2-dimethyl-5,6,8,9-tetrahydroarachidonic acid.

EXAMPLE 15

By substituting an equivalent quantity of γ-linolenic acid in the procedure of Example 6 and subsequently following the procedures of Example 6-14, there is obtained methyl 2,2-dimethyl-5,6-dihydroarachidonate.

What is claimed is:
1. A compound of the formula

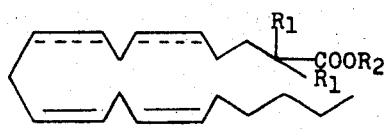

wherein $R_1$ is lower alkyl having 1–7 carbon atoms inclusive, $R_2$ is hydrogen or lower alkyl having 1–7 carbon atoms inclusive, and the dotted lines represent optional double bonds.

2. As in claim 1, a compound of the formula

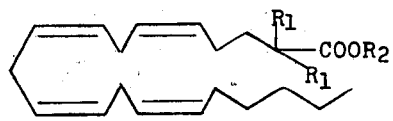

wherein $R_1$ is lower alkyl having 1–7 carbon atoms inclusive and $R_2$ is hydrogen or lower alkyl having 1–7 carbon atoms inclusive.

3. As in claim 1, a compound wherein $R_2$ is lower alkyl.

4. As in claim 1, a compound wherein $R_2$ is hydrogen.

5. As in claim 1, the compound which is 2,2-dimethylarachidonic acid.

6. As in claim 1, the compound which is methyl 2,2-dimethylarachidonate.

7. As in claim 1, the compound which is ethyl 2,2-dimethylarachidonate.

* * * * *